United States Patent [19]

Clark et al.

[11] 4,440,564

[45] Apr. 3, 1984

[54] HETEROCYCLIC PENTALENES AS HERBICIDES

[75] Inventors: Michael T. Clark; Ian J. Gilmore, both of Sittingbourne, England

[73] Assignee: Shell Oil Company, Houston, Tex.

[21] Appl. No.: 418,369

[22] Filed: Sep. 15, 1982

Related U.S. Application Data

[63] Continuation-in-part of Ser. No. 388,777, Jun. 15, 1982, abandoned.

[30] Foreign Application Priority Data

Jun. 24, 1981 [GB] United Kingdom .................. 8119403

[51] Int. Cl.$^3$ ............................................. A01N 43/02
[52] U.S. Cl. ..................................................... 71/90
[58] Field of Search ............................. 71/90; 548/122

[56] References Cited

U.S. PATENT DOCUMENTS 3,182,068  5/1965  Sasse et al. ........................... 548/122
4,179,441  12/1979  Moore ...................................... 71/90
4,289,524  9/1981  Belkind .................................... 71/90

OTHER PUBLICATIONS

Perrier et al., "Sulfur-Containing, etc.," (1979), CA 91, No. 74534c, (1979).
Beer et al., "A Derivative, etc.," (1972), Tetra. Lett. 18, pp. 1835–1836, (1972).

*Primary Examiner*—Glennon H. Hollrah

[57] ABSTRACT

Use as herbicides of, and herbicidal compositions containing as active ingredients, compounds of the formula:

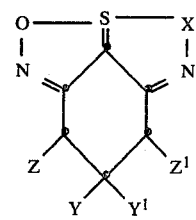

wherein the symbols have assigned meanings.

2 Claims, No Drawings

HETEROCYCLIC PENTALENES AS HERBICIDES

This application is a continuation-in-part of application Ser. No. 388,777, filed on June 15, 1982, now abandoned.

DESCRIPTION OF THE INVENTION

It has been found that certain oxadithiadiazo- and oxathiaoxadiazo-2,5-pentalenes have useful herbicidal properties. These compounds are characterized by the general formula:

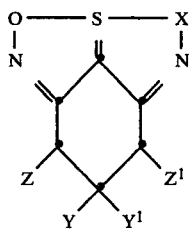
(I)

wherein X is O or S, and Z, $Z^1$, Y and $Y^1$ each is hydrogen or alkyl of from one to three carbon atoms.

The invention also provides a process for the preparation of compounds of Formula I which comprises treating a dioxime of the general formula

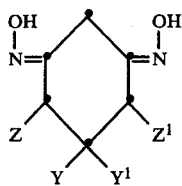
(II)

with sulphur monochloride and/or sulfur dichloride. The product of this reaction is typically a mixture of the desired oxadithiadiaza-2,5-pentalene of Formula I (wherein X is a sulphur atom) and the desired oxathiaoxadiaza-2,5-pentalene of Formula I (wherein X is an oxygen atom). The ratio in which these two products form during the reaction is rather variable depending on the chemical make up of the dioxime starting material used and the type of sulfur chloride employed. Typically when sulfur dichloride rather than sulfur monochloride, the yield of oxathiaoxadiaza-2,5-pentalene is enhanced. The reaction is suitably conducted in a polar organic solvent such as tetrahydrofuran or diethyl ether, which is inert under the reaction conditions employed. The reaction temperature will typically range between −80° and −20° C. When the reaction is carried out in batch fashion it is desirable to slowly add the sulphur chloride reactant to the dioxime in the polar organic solvent at a temperature of from −80° to −20° C., to maintain this temperature for a time interval, for example 8 to 12 hours, and then to allow the reaction mixture to warm slowly to ambient temperature (20° C.), holding it at this temperature for an additional 6 to 16 hours. Generally the total reaction time will range between 16 and 30 hours.

As noted previously, the reaction product of the reaction between the dioxime of Formula II and a sulphur chloride generally contains a mixture of the two compounds of Formula I which are identical in structure except for the nature of the X substituent. The desired oxadithiadiaza-2,5-pentalene component and the oxathiaoxadiaza-2,5-pentalene component are suitably separated from the mixed reaction product using conventional techniques. In a preferred separation process, the two components in the reaction product are isolated by chromatography on silica using an eluant such as petroleum/ether or methylene chloride. After isolation, the components can be further purified using conventional solvent recrystallization techniques, alcohols such as ethanol and hydrocarbon solvents such as hexane, cyclohexane and benzene being suitable recrystallization solvents.

The dioximes of Formula II are generally known compounds, being prepared by reaction of the appropriate beta-diketone of the formula

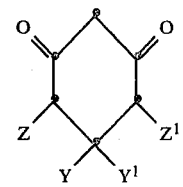
(III)

with hydroxylamine. This reaction is typically carried out by reacting stoichiometric amounts of the diketone (1 mole) and hydroxylamine (2 moles) at temperature of from 25° to 100° C. for 10 to 60 minutes in a polar solvent.

The precursor β-diketones (III) are known compounds which may be obtained by a variety of conventional synthetic techniques. For example, they are suitably prepared by condensation of the appropriate ester, diester or ketoester with a methyl alkenyl ketone followed by cyclization of the resulting saturated ketoester. Alternatively, the carbon-carbon double bond may be in the ester reactant and a methyl alkyl ketone may be employed. These condensations and ring closure reactions are typically carried out in the presence of a base such as sodium ethoxide or sodium hydride.

Preparation of typical individual species of the compounds of Formula I is described in the following examples. In each case, the identity of each product and each intermediate was confirmed by appropriate chemical and spectral analyses.

EXAMPLE 1

Preparation of (a) 7,8-dihydro-6H-(1,2,5)oxathiazolo(4,3,2-hi)(2,1,3)benzoxathiazole-3-$S^{IV}$ (1) (Formula I, X=O, Z=H, $Z^1$=H, Y=H, $Y^1$=H). and (b) 7,8-dihydro-6-H(1,2,3)dithiazolo(4,5,1-hi)(2,1,3)benzoxathiazole-3-$S^{IV}$ (2) (Formula I, X=S, Z=H, $Z^1$=H, Y=H, $Y^1$=H).

20.0 g of 1,3-cyclohexane dioxime was suspended in 750 ml of dry tetrahydrofuran and the temperature of the mixture was lowered to −70° C. with stirring in an acetone-dry ice bath. 39.0 g of sulphur monochloride was added dropwise with stirring and the temperature was maintained at −70° C. for an additional 12 hours. The reaction mixture was then allowed to warm to room temperature and was poured into water. The aqueous mixture was extracted with chloroform and the chloroform extract was dried over sodium sulphate. The dried mixture was chromatographed over silica, eluting with chloroform. The first fraction, made up of sulphur, was discarded. A second orange fraction was collected, the eluent was evaporated and the orange residue was recrystallized from cyclohexane to give 1, as orange needles, m.p.: 66°–67° C.

A third, brown, fraction was collected, the eluent evaporated, and the black/brown residue was recrystallized from cyclohexane to give 2, as brown needles, m.p.: 154°–155° C.

EXAMPLE 2

Alternative preparation of 1 and 2.

5.4 g of 1,3-cyclohexanone dioxime was suspended in sodium-dried tetrahydrofuran and the temperature of the mixture was lowered to −70° C. in an acetone-dry ice bath. The mixture was stirred vigorously and 8.0 g of sulphur dichloride was added dropwise while the temperature was maintained at −70° C. The mixture was then stirred for an additional 8 hours at −70° C. and then allowed to warm at room temperature with continued stirring for 24 hours. The reaction mixture was then poured into 500 ml of cold water and extracted with hot toluene. The extract was dried over sodium sulphate, filtered and the solvent removed by distillation under reduced pressure. The residue was chromatographed over silica gel, elution with chloroform giving an orange-yellow solid followed by a second fraction of a dark orange solid; both fractions were recrystallized from cyclohexane to afford, respectively, (1) m.p.: 65°–66° C., and (2) m.p.: 158°–159° C.

EXAMPLE 3

Preparation of (a) 7,8-dihydro-7,7-dimethyl-6H-(1,2,5)oxathiazolo(4,3,2-hi)(2,1,3)benzoxathiazole-3-$S^{IV}$ (3) (Formula I, X=O, Z=H, $Z^1$=H, Y=—$CH_3$, $Y^1$=—$CH_3$) and (b) 7,8-dihydro-7,7-dimethyl-6H-(1,2,3)dithiazolo(4,5,1-hi)(2,1,3)benzothiazole-3-$S^{IV}$ (4) (Formula I, X=S, Z=H, $Z^1$=H, Y=—$CH_3$, $Y^1$=—$CH_3$)

25.5 g of dimedone dioxime was suspended in dry tetrahydrofuran and maintained at −70° C. to −80° C. in an acetone-dry ice bath with stirring. Subsequently, sulphur monochloride was added dropwise to the stirred mixture and it was held for an additional 12 hours at −70° to −80° C. with stirring. The reaction mixture was then allowed to warm to room temperature and held for an additional 48 hours. The reaction mixture was then poured into 1500 ml of water and the resulting mixture was extracted with hot toluene. The toluene extract was filtered with glass wool to remove any sulphur-containing solids, dried over sodium sulphate and the toluene solvent was removed under vacuum. The residue was chromatographed on silica, first with toluene to obtain an orange solid, and then with chloroform to obtain a black/orange solid. The orange solid was recrystallized from hexane to give 3, as orange platelets, m.p.: 65.6° C. The black/orange solid was recrystallized from cyclohexane to give 4 as black iridescent needles, m.p.: 97° C.

EXAMPLE 4

Alternative preparation of 3 and 4

8.5 g of dimedone dioxime was suspended in 200 ml of dry tetrahydrofuran at −60° C. in an acetone-dry ice bath and 5.65 g of sulphur dichloride was added dropwise with vigorous stirring to give a yellowish-orange solution. This solution was stirred at −60° to −70° C. for 8 hours after which it was warmed to room temperature and held for an additional 36 hours with stirring. The solution was poured into water and extracted with toluene by refluxing portions of the aqueous mixtures with toluene. The toluene extracts were combined and dried over magnesium sulphate. The toluene was removed by evaporation in a vacuum and the residue was chromatographed on silica gel eluting first with toluene and then with chloroform. The first fraction, eluted with toluene, gave an orange solid which was recrystallized from hexane to give 3, as orange needles, m.p.: 64°–65° C. The second fraction, eluted with chloroform, gave a dark orange/black solid which was recrystallized from cyclohexane to give 4, as black crystals, m.p.: 98°–100° C.

EXAMPLE 5

Preparation of (a) 7,8-dihydro-6,8-dimethyl-6H-(1,2,5)oxathiazolo(4,3,2-hi)(2,1,3)benzoxathiazole-3-$S^{IV}$ (5) (Formula I, X=O, Z=—$CH_3$, $Z^1$=—$CH_3$, Y=H, $Y^1$=H) and (b) 7,8-dihydro-6,8-dimethyl-6H-(1,2,3)dithiazolo(4,5,1-hi)(2,1,3)benzoxathiazole-3-$S^{IV}$ (6) (Formula I, X=S, Z=—$CH_3$, $Z^1$=—$CH_3$, Y=H, $Y^1$=H)

11.9 g of 4,6-dimethyl-1,3-cyclohexanone dioxime was suspended in 350 ml of dry tetrahydrofuran and cooled in an acetone-dry ice bath to −70° C., when 20.25 g of sulphur monochloride was added dropwise with stirring. The reaction mixture was then stirred vigorously at −70° C. for an additional 12 hours, after which it was allowed to warm to room temperature and held for 24 hours. The reaction mixture was then poured into water and extracted with hot toluene. The toluene extract was dried with magnesium sulphate and the solvent was removed by evaporation in a vacuum. The residue was chromatographed on silica, eluting with chloroform. The first fraction, made up of sulphur, was discarded. The second fraction, pale yellow in color, was collected and recrystallized from petroleum ether (b.p. 40°–60° C.) to give 5 as pale orange needles, m.p.: 92°–93° C. The third fraction, deep orange in color, was collected and recrystallized from cyclohexane to give 6, as dark brown orange needles, m.p.: 113°–114° C.

EXAMPLE 6

Alternative preparation of 5 and 6

13.6 g of 4,6-dimethyl-1,3-cyclohexanone dioxime was suspended in dry tetrahydrofuran and the mixture was cooled to −65° C. in an acetone-dry ice bath with stirring. 17.9 g of sulphur dichloride was added dropwise to the cooled mixture and the resulting solution was stirred for 18 hours at −65° to −70° C. The reaction mixture was allowed to warm to room temperature and poured into water. The aqueous mixture was extracted with chloroform, the extract dried over magnesium sulphate and chromatographed over silica, eluting with chloroform. The first fraction, consisting essentially of sulphur, was discarded; the second and third fractions, being yellow and brown/black in color, respectively, were collected and recrystallized from ethanol. The second fraction was 5, m.p.: 97°–99° C., while the third fraction was 6, m.p.: 110°–112.5° C.

EXAMPLES 7 AND 8

By methods analogous to those described in Examples 1–6, the two individual species of Formula I given in Table I were prepared.

TABLE I

| Compound No. | X | Z | Z¹ | Y | Y¹ | m.p.: (°C.) |
|---|---|---|---|---|---|---|
| 7 | O | H | H | H | —CH₃ | 54–55 |
| 8 | S | H | H | H | —CH₃ | 136.5 |

The compounds of Formula I have useful herbicidal properties and the invention provides a method for combating undesired plant growth at a locus, which comprises applying to the locus an effective dosage of a compound of Formula I. Likewise, the invention includes plant growth control compositions comprising an inert carrier or a surface-active agent, or both a carrier and a surface-active agent, and, as active ingredient at least one compound of Formula I.

A carrier in a composition according to the invention is any inert material with which the active ingredient is formulated to facilitate application to the locus to be treated, which may for example be a plant seed or soil, or to facilitate storage, transport or handling. A carrier may be a solid or a liquid, including a material which is normally gaseous but which has been compressed to form a liquid, and any of the carriers normally used in formulating herbicidal compositions may be used.

Suitable solid carriers are natural and synthetic clays and silicates, for example, natural silicas such as diatomaceous earth; magnesium silicates, for example, talcs, magnesium aluminum silicates, for example, attapulgites and vermiculites; aluminum silicates, for example, kaolinites, montmorillonites and micas; calcium carbonates; calcium sulfate; synthetic hydrated silicon oxides and synthetic calcium or aluminum silicates; elements such as, for example, carbon and sulfur; natural and synthetic resins such as, for example coumarone resins, polyvinyl chloride and styrene polymers and copolymers; bitumen, waxes such as, for example, beeswax, paraffin wax, and chlorinated minerals waxes; and solid fertilizers, for example, superphosphates.

Examples of suitable fluid carriers are water, dimethyl sulfoxide, alcohols, such as, for example, methanol, isopropyl alcohol, glycols; ketones such as for example, acetone, methyl ethyl ketone, methyl isobutyl ketone, isophorone and cyclohexanone; ethers such as, for example, cellosolves; aromatic hydrocarbons such as, for example, benzene, toluene and xylene; petroleum fractions such as, for example, herosene, light mineral oils; chlorinated hydrocarbons, such as, for example, carbon tetrachloride, perchloroethylene, trichloroethane, including liquefied normall vaporous gaseous compounds. Mixtures of different liquids are often suitable. The surface-active agent may be an emulsifying agent or a dispersing agent or a wetting agent; it may be nonionic or ionic any of the surface-active agents usually applied in formulating herbicides or insecticides may be used. Examples of suitable surface-active agents are sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil and sodium alkyl-aryl sulfonates such as sodium dodecylbenzene sulfonate; and polymers of ethylene oxide and copolymers of ethylene oxide and propylene oxides.

The compositions may be formulated as wettable powders, dusts, granules, solutions, emulsifiable concentrates, emulsions, suspension concentrates and aerosols. Wettable powders are usually compounded to contain 25, 50 or 75% by weight of toxicant and usually contain in addition to solid carrier, 3–10% by weight of a dispersing agent, 15% of a surface-active agent and where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing ½–10% by weight of toxicant. Granules are usually prepared to have a size between 10 and 100 BS mesh (1.676–0.152 mm), and may be manufactured by agglomeration or impregnation techniques. Generally, granules will contain ½–25% by weight toxicant and 0–1% by weight of additives such as stabilizers, slow release modifiers and binding agents. Emulsifiable concentrates usually contain, in addition to the solvent and, when necessary, cosolvent, 10–50% weight per volume toxicant, 2–20% weight per volume emulsifiers and 0–20% weight per volume of appropriate additives such as stabilizers, penetrants and corrosion inhibitors. Suspension concentrates are compounded so as to obtain a stable, non-sedimenting flowable product and usually contain 10–75% weight toxicant, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also like within the scope of the present invention. The said emulsions may be of the water-in-oil or of the oil-in-water type, and may have a thick mayonnaise-like consistency.

The compositions may also contain other ingredients, for example, other compounds possessing pesticidal, especially insecticidal, acaricidal, herbicidal or fungicidal properties.

Protection of a locus or area from unwanted plants is effected by applying a compound of Formula I, ordinarily in a composition of one of the aforementioned types, to the soil in which seeds of the unwanted plants are present, or to the foliage of the plants. The active compound, of course, is applied in an amount sufficient to exert the desired action.

The amount of the compound of Formula I to be used in controlling undesired plants will naturally depend on the condition of the plants, the degree of activity desired, the formulation used, the mode of application, the climate, the season of the year, and other variables. Recommendations as to precise amounts are, therefore, not possible. In general, however, application to the locus to be protected of from 0.02 to 10.0, preferably from 0.1 to 5, kilograms, per hectare of the compound of Formula I will be satisfactory.

Herbicidal Activity

To evaluate their herbicidal activity in compositions according to the invention, compounds of the previous examples were tested using as a representative range of plants: maize, Zea mays (MZ); rice, Oryza sativa (R); barnyard grass, Echinochloa crusgalli (BG); oat, Avena sativa (O); linseed, Linum usitatissimum (L); mustard, Sinapis alba (M); sugar beet, Beta vulgaris (SB) and soya bean, Glycine max (S).

The tests fall into two categories, preemergence and postemergence. The preemergence tests involved spraying a liquid formulation of the compound onto the soil in which the seeds of the plant species mentioned above had recently been sown. The postemergence tests involved two types of test, viz., soil drench and foliar spray tests. In the soil drench tests the soil in which the seedling plants of the above species were growing, was drenched with a liquid formulation containing a compound of the invention, and in the foliar spray tests the seedling plants were sprayed with such a formulation.

The soil used in the tests was a prepared horticultural loam.

The formulations used in the tests were prepared by diluting with water, solutions of the test compounds in acetone containing 0.4% by weight of an alkylphenol-/ethylene oxide condensate available under the trade name Triton X-155. The acetone solutions were diluted with water and the resulting formulations applied typically at dosage levels corresponding to 5 kg and/or 1 kg of active material per hectare in a volume equivalent to 650 liters per hectare in the soil spray and foliar spray tests, and at a dosage level equivalent to 10 kilograms of active material per hectare in a volume equivalent to approximately 3,000 liters per hectare in the soil drench tests.

In the preemergence tests untreated sown soil and in the postemergence tests untreated soil bearing seedlings plants were used as controls.

The herbicidal effects of the test compounds were assessed visually eleven days after spraying in the foliage and drenching the soil and twelve days after spraying the soil, and were recorded on a 0–9 scale. A rating 0 indicates growth as untreated control, a rating 9 indicates death. An increase of 1 unit on the linear scale approximately to a 10% increase in the level of effect.

The results of the tests are set out in Table II.

TABLE II

| Compound No. | Soil Drench 10 kg/ha | | | | | | | | Dosage kg/ha | Foliar Spray | | | | | | | | Preemergence | | | | | | | |
|---|---|---|---|---|---|---|---|---|---|---|---|---|---|---|---|---|---|---|---|---|---|---|---|---|---|
| | MZ | R | BG | O | L | M | SB | S | | MZ | R | BG | O | L | M | SB | S | MZ | R | BG | O | L | M | SB | S |
| 1 | 6 | 7 | 9 | 7 | 9 | 9 | 7 | 5 | 5 | 5 | 5 | 8 | 6 | 9 | 9 | 9 | 8 | 3 | 7 | 9 | 3 | 4 | 5 | 5 | 2 |
| | | | | | | | | | 1 | 3 | 3 | 6 | 3 | 6 | 7 | 7 | 6 | 0 | 4 | 5 | 2 | 2 | 2 | 0 | 0 |
| 2 | 3 | 3 | 4 | 3 | 6 | 7 | 8 | 5 | 5 | 2 | 5 | 6 | 3 | 9 | 9 | 9 | 7 | 2 | 3 | 4 | 0 | 2 | 3 | 6 | 2 |
| | | | | | | | | | 1 | 1 | 3 | 4 | 2 | 8 | 9 | 9 | 6 | 0 | 0 | 0 | 0 | 0 | 0 | 0 | 0 |
| 3 | 5 | 2 | 3 | 3 | 2 | 5 | 5 | 1 | 5 | 3 | 5 | 9 | 6 | 9 | 9 | 9 | 7 | 2 | 5 | 7 | 0 | 3 | 3 | 7 | 2 |
| | | | | | | | | | 1 | 2 | 1 | 8 | 1 | 4 | 6 | 6 | 5 | 0 | 0 | 2 | 0 | 0 | 0 | 4 | 0 |
| 4 | 0 | 4 | 0 | 0 | 9 | 7 | 6 | 0 | 5 | 5 | 7 | 7 | 6 | 9 | 9 | 9 | 9 | 0 | 0 | 5 | 5 | 4 | 2 | 3 | 4 |
| | | | | | | | | | 1 | 3 | 4 | 4 | 2 | 7 | 8 | 9 | 9 | 0 | 0 | 0 | 0 | 0 | 0 | 0 | 4 |
| 5 | 9 | 8 | 9 | 7 | 9 | 9 | 9 | 9 | 5 | 6 | 6 | 9 | 7 | 8 | 9 | 9 | 8 | 4 | 8 | 8 | 3 | 4 | 7 | 9 | 6 |
| | | | | | | | | | 1 | 2 | 0 | 5 | 3 | 6 | 8 | 8 | 4 | 1 | 2 | 2 | 0 | 0 | 2 | 3 | 0 |
| 6 | 0 | 0 | 2 | 0 | 6 | 4 | 8 | 0 | 5 | 4 | 7 | 6 | 5 | 9 | 9 | 9 | 8 | 0 | 0 | 6 | 0 | 6 | 4 | 7 | 2 |
| | | | | | | | | | 1 | 0 | 5 | 5 | 4 | 8 | 9 | 9 | 7 | 0 | 0 | 2 | 0 | 0 | 0 | 0 | 0 |
| 7 | 7 | 7 | 6 | 6 | 8 | 9 | 9 | 3 | 5 | 5 | 4 | 9 | 6 | 8 | 9 | 9 | 8 | 5 | 0 | 7 | 3 | 4 | 6 | 3 | 4 |
| | | | | | | | | | 1 | 4 | 3 | 8 | 4 | 7 | 8 | 8 | 5 | 0 | 0 | 3 | 0 | 0 | 3 | 0 | 2 |
| 8 | 0 | 0 | 2 | 0 | 2 | 3 | 9 | 0 | 5 | 6 | 7 | 9 | 5 | 9 | 9 | 9 | 9 | 0 | 0 | 7 | 0 | 5 | 0 | 6 | 0 |
| | | | | | | | | | 1 | 4 | 5 | 6 | 2 | 7 | 8 | 9 | 7 | 0 | 0 | 0 | 0 | 0 | 0 | 0 | 0 |

We claim:

1. A method for controlling unwanted plant growth at a locus, which comprises treating the locus with an effective dosage of a compound of the formula:

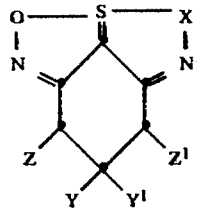

wherein X is O or S, and Z, $Z^1$, Y and $Y^1$ each is hydrogen or alkyl of from one to three carbon atoms.

2. A method according to claim 1 wherein Z, $Z^1$, Y and $Y^1$ each is hydrogen or methyl.

* * * * *